United States Patent [19]
Ishihara et al.

[11] Patent Number: 5,722,398
[45] Date of Patent: Mar. 3, 1998

[54] APPARATUS FOR MEASURING CONCENTRATION OF HEMOGLOBIN AND METHOD FOR THE SAME

[75] Inventors: Ken Ishihara; Kaoru Asano; Yasunori Maekawa, all of Hyogo, Japan

[73] Assignee: TOA Medical Electronics Co., Ltd., Hyogo, Japan

[21] Appl. No.: 557,573

[22] Filed: Nov. 14, 1995

[30] Foreign Application Priority Data

Nov. 15, 1994 [JP] Japan ................... 6-280936

[51] Int. Cl.$^6$ ........................................ A61B 5/00
[52] U.S. Cl. ........................................ 128/633
[58] Field of Search ........................ 128/633, 637, 128/664, 665; 356/39

[56] References Cited

U.S. PATENT DOCUMENTS 4,998,533  3/1991  Winkelman ................. 128/637

FOREIGN PATENT DOCUMENTS 2-95262   4/1990   Japan.
9221283  12/1992   WIPO.
9311701   6/1993   WIPO.

*Primary Examiner*—Jennifer Bahr
*Assistant Examiner*—Eric F. Winakur

[57] ABSTRACT

An apparatus for measuring a concentration of hemoglobin includes a light application device for applying light to a detection region containing a blood vessel present in a living body; an image capturing device for capturing an image of the detection region to which the light is applied; and an analyzer for analyzing the concentration of hemoglobin in blood flowing through the blood vessel by processing the captured image. The analyzer includes a light intensity detector for detecting a light intensity of a body tissue and a light intensity of blood using the captured image. It further includes a calculator for calculating the concentration of hemoglobin from a ratio of the light intensity of the body tissue relative to the light intensity of blood thus detected.

8 Claims, 4 Drawing Sheets

Nº 5,722,398

APPARATUS FOR MEASURING CONCENTRATION OF HEMOGLOBIN AND METHOD FOR THE SAME

BACKGROUND OF THE INVENTION

1. Field of the Invention

The present invention relates to an apparatus for analyzing blood in a non-invasive manner and a method for doing the same. More particularly, it relates to an apparatus for measuring a concentration of hemoglobin in blood without collecting or isolating it and a measuring method using the same.

2. Description of Related Art

A conventional apparatus for measuring in vivio, a concentration of hemoglobin is utilized by applying a plurality of light beams each having a different wavelength to a living body. By substituting the values thus obtained with respect to each wavelength, in the equation of modified Lambert-Beer's law as below, a concentration C of hemoglobin or an amount $\Delta C$ of change of the concentration of hemoglobin can be determined from solutions of simultaneous equations (see, for example, Japanese Unexamined Patent Publication No. HEI 2(1990)-95262). The equation is:

$$\log (Io/I) = \epsilon CD + S \qquad (1)$$

where Io represents an intensity of incident light, I represents an intensity of transmitted light (intensity of reflection light), S represents a living body scattering term, $\epsilon$ represents an absorption coefficient and D represents a thickness of a blood layer.

The above conventional apparatus, however, has suffered from such problems that a light source is required which applies a plurality of light beams, each having a different wavelength, individually upon a living body and that the values obtained upon measurement need to be calibrated depending on an intensity of the incident light.

SUMMARY OF THE INVENTION

The present invention has been conceived in view of the above circumstances. Thus, an object of the present invention is to provide an apparatus and method for measuring a concentration of hemoglobin using a light source having one wavelength (or one wavelength band) and eliminating the need of calibrating the concentration depending on an intensity of incident light.

In one aspect, the present invention provides an apparatus for measuring a concentration of hemoglobin comprising: light application means for applying light to a detection region containing a blood vessel present in a living body; imaging means for capturing an image of the detection region to which the light is applied; and analysis means for analyzing the concentration of hemoglobin in blood flowing through the blood vessel by processing the captured image, the analysis means comprising light intensity detection means for detecting a light intensity of a body tissue and a light intensity of blood using the captured image and calculating means for calculating the concentration of hemoglobin from a ratio of the light intensity of the body tissue relative to the light intensity of blood thus detected.

In another aspect, the present invention provides a method comprising the steps of: applying light to a detection region containing a blood vessel present in a living body, capturing an image of the detection region to which the light is applied, and processing the captured image to measure a concentration of hemoglobin, the step of processing the captured image comprising the steps of detecting a light intensity of a body tissue and a light intensity of blood using the captured image and calculating the concentration of hemoglobin from a ratio of the light intensity of the body tissue relative to the light intensity of blood thus detected.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
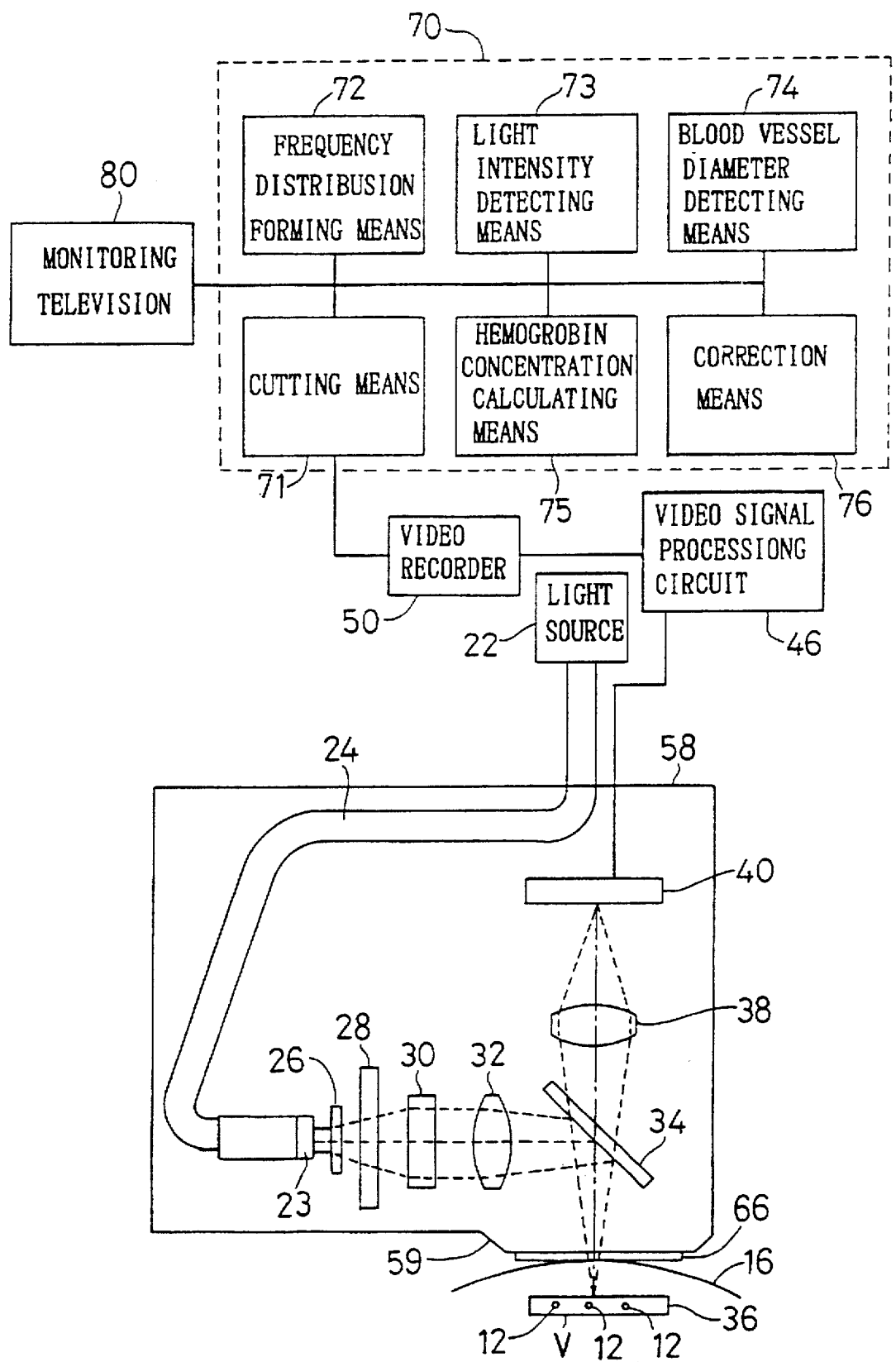
FIG. 1 is a view showing the structure of an embodiment of the present invention.

The present invention will be detailed in conjunction with a preferred embodiment, which is not intended to limit the scope of the present invention.

The apparatus is directed to measuring a concentration of hemoglobin in blood present in a living body in a non-invasive manner. The living body is preferably that of mammals including human bodies.

Detection region, wherein the light application device applies light to a detection region containing the blood vessel present in the living body, preferably refers to a predetermined region containing the blood vessel that is present as it is in the living body, and does not refer to a part of the living body that is surgically removed in vitro.

The thickness of the blood vessel contained in a subject region is not limited, but a capillary or small arteries and veins located near as a skin are preferable to produce a good result in reproduction. Incidentally, blood information obtained in capillary or small arteries and veins can be translated into information for thick vessels (medium-size or large arteries and veins).

Light intensity of the body tissue refers to a light intensity emitted from a portion of the body tissue which thus is a light intensity transmitted through or reflected from the body tissue; and the light of intensity of blood is similarly understood.

As an example of the light application means of the present invention, either a continuous or an intermittent light source may be used; a continuous light source that continuously applies light to the detection region includes a laser, a halogen lamp or a tungsten lamp while a intermittent light source that applies light intermittently to the detection region includes a pulse laser (for example, 7000 series manufactured by Spectra-Physics Co., Ltd.) and a flash lamp (for example, DSX series manufactured by Sugawara Laboratories, Inc., Japan).

In addition to one of the above light sources the light application means preferably further includes (1) an optical fiber, (2) a reflector, (3) a lens, (4) a slit or the like, all of which allow light from the light source to be properly directed to the detection region. Alternatively, appropriate combinations such as those of (1) and (2); (1) and (3); (1), (2) and (3); (1), (2), (3) and (4); (2) and (3); and (2), (3) and (4) may be incorporated in the light application means.

In this case, the reflector may be replaced with a prism. In particular, the light application means may include a polarizing device for applying polarizing light to the detection region.

An example of the image capturing means of the present invention is a general CCD image sensor.

In an optical system for allowing the reflected light from the detection region to be directed to the CCD image sensor, the imaging means may include an optical fiber, various kinds of reflectors, a polarizing element, a lens of each kind, a prism, a slit or a filter, and preferably include, if the reflection light from the detection region is faint, an image intensifier. The image capturing means may further include a polarizing device for removing unnecessary scattered light emitted from the detection region.

Desirably, the image capturing means may include, in its signal processing system, a video signal processing circuit for processing, as video signals, output signals from each pixel of the CCD image sensor while supplying scanning signals to the CCD image sensor, and a VTR, a laser disc recorder, or other such recorder for recording the video signals.

The light application means and image capturing means may be included within a commercially available video microscope system.

An example of an analysis means may be a commercially available personal computer (for example, Power Mac manufactured by Apple Computer Inc.).

The analysis means may further include blood diameter detecting means for detecting a diameter of the blood vessel obtained in the captured image and correction means for correcting the concentration of hemoglobin based on the detected diameter of the blood vessel.

Preferably the calculating means includes means for calculating the concentration C of hemoglobin from the following equation:

$$C = K \cdot \log (I_T/I_B)$$

where C represents a concentration of hemoglobin, $I_T$ a light intensity of a body tissue, $I_B$ a light intensity of blood and K a constant.

Preferably the light intensity detecting means includes means for examining a frequency distribution on intensity of pixels in the captured image and means for detecting, when the frequency distribution shows peak values at intensity A and B (A<B), the luminance A as the light intensity of blood and the intensity B as the light intensity of the body tissue.

The light intensity detecting means of the present invention detects the light intensity $I_T$ of the blood tissue and the light intensity $I_B$ of body from the image obtained with the imaging means.

By the way, C=0 is obtained with respect to a portion of the body tissue. Then the equation (1) produces the following equation:

$$\log (I_0/I_T) = S \quad (2)$$

With respect to blood, the equation is given:

$$\log (I_0/I_B) = \epsilon CD + S \quad (3)$$

Subtracting the equation (2) from the equation (3) produces the following equation:

$$\log (I_T/I_B) = \epsilon CD \quad (4)$$

Here D represents a thickness of a blood layer which is a constant determined by the diameter of the blood vessel. This value can be corrected depending on the diameter obtained in the image. In addition, $\epsilon$ is a constant determined depending on wavelength of light incident upon the detection region.

Accordingly, the calculating means can calculate the concentration C of hemoglobin from the equation (4).

In another aspect, the present invention provides a method comprising the steps of: applying light to a detection region containing a blood vessel present in a living body, capturing an image of the detection region to which the light is applied, and processing the captured image to measure a concentration of hemoglobin, the step of processing the captured image comprising the sub-steps of detecting a light intensity of a body tissue and a light intensity of blood using the captured image and calculating the concentration of hemoglobin from a ratio of the light intensity of the body tissue relative to the light intensity of blood thus detected.

The step of calculating the concentration of hemoglobin may further comprise the sub-steps of detecting the diameter of the blood vessel obtained in the captured image and correcting the calculated concentration of hemoglobin based on the detected diameter of the blood vessel.

The step of calculating the concentration of hemoglobin may comprise a step of calculating the following equation:

$$C = K \cdot \log (I_T/I_B)$$

where C represents a concentration of hemoglobin, $I_T$ a light intensity of a blood tissue, $I_B$ a light intensity of blood and K a constant.

Preferably the step of detecting the light intensities of the body tissue and the blood comprises detecting, when a frequency distribution on intensity of pixels in the captured image shows peak values at intensity A and B (A<B), the A as the light intensity of blood and the intensity B as the light intensity of the body tissue.

These and other objects of the present application will become more readily apparent from the detailed description given hereinafter. However, it should be understood that the detailed description and specific examples, while indicating a preferred embodiment of the invention, are given by way of illustration only, since various changes and modifications within the spirit and scope of the invention will become apparent to those skilled in the art from this detailed description.

FIG. 1 is a view illustrating a preferred embodiment of the present invention.

Light emitted from a light source 22 of a halogen lamp is applied to a diffuser 26 via an optical fiber 24 and a filter 23. The light is scattered by the diffuser 26 and uniformly applied to a plate 28. Thus, the plate 28 substantially serves as a light-emitting face such that a real image 36 is formed thereon via an optical system comprising lenses 30 and 32 and a beam splitter 34, such as a dichroic mirror, the real image 36 traversing blood vessels 12 that exist inside of a skin surface 16 of a living body. The filter 23 preferably has a center wavelength of 550 nm and a half width of 40 nm. The plate 28 may be a light diffusing board, for example that of a frost type manufactured by Sigma Optical Materials Co., Ltd.

The region of the real image 36 on the plate 28 including the blood vessels 12 is referred to as a region V. The reflection light from the region V is received by a CCD 40 via the beam splitter 34 and a lens 38.

The filter 23, the diffuser 26, the plate 28, the lenses 30, 32 and 38, the beam splitter 34 and the CCD 40 are all accommodated in a probe 58. The probe 58 has a tip 59 allowed to closely contact the skin surface 16 via a transparent plate 66 made of plastic or glass to give a stable image free from being shifted. Image signals output from each pixel of the CCD 40 are processed by a video signal processing circuit 46. The video signal processing circuit 46 successively forms one frame image per one thirtieth of a second, and the frame images thus formed are sequentially recorded in a video recorder (for example, a laser disk recorder) 50.

Reference numeral 70 denotes analysis means for analyzing blood flowing through the blood vessels 12 contained in the detection region V by processing the captured image. The analysis means 70 can be, for example, a commercially available personal computer.

The analysis means 70 comprises cutting means 71 for cutting (trimming) a predetermined region of the image output from a video recorder 50; frequency distribution forming means 72 for forming a frequency distribution curve (histogram) on the intensity of each pixel of the cut predetermined region; light intensity detecting means 73 for detecting, when a frequency distribution curve shows maximum values at A and B (A<B), the intensity A as a light intensity $I_B$ of blood and the intensity B as a light intensity $I_T$ of a body tissue; blood vessel diameter detecting means 74 for detecting, with the light intensities, the diameter D of the blood vessel contained in the predetermined region of the cut image; hemoglobin concentration calculating means 75 for calculating the concentration of hemoglobin based on the light intensities $I_B$ and $I_T$ and the diameter D of the blood vessel; and correction means 76 for correcting, if necessary, the concentration of hemoglobin thus calculated. Each image or histogram formed in the analysis means 70 can be monitored by a monitoring device such as television 80 for example.

Figure 2:
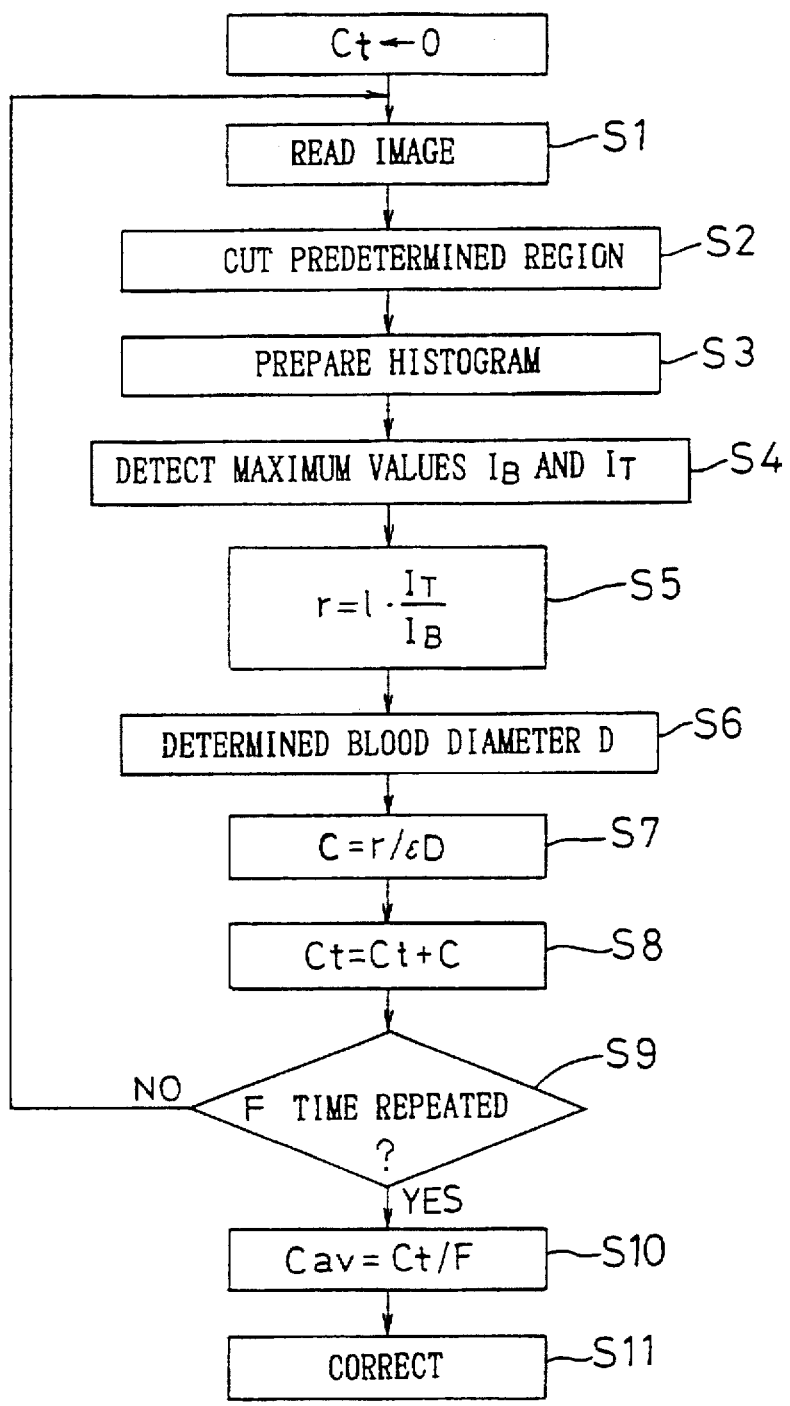
FIG. 2 is a flowchart showing the operation of the embodiment.

The flowchart of FIG. 2 illustrates a preferred procedure of calculation of the concentration of hemoglobin using the analysis means 70 which will be explained hereinafter.

The analysis means 70 processes a plurality of frames or fields of images recorded in time series in the video recorder 50, by reading them sequentially.

Figure 3:
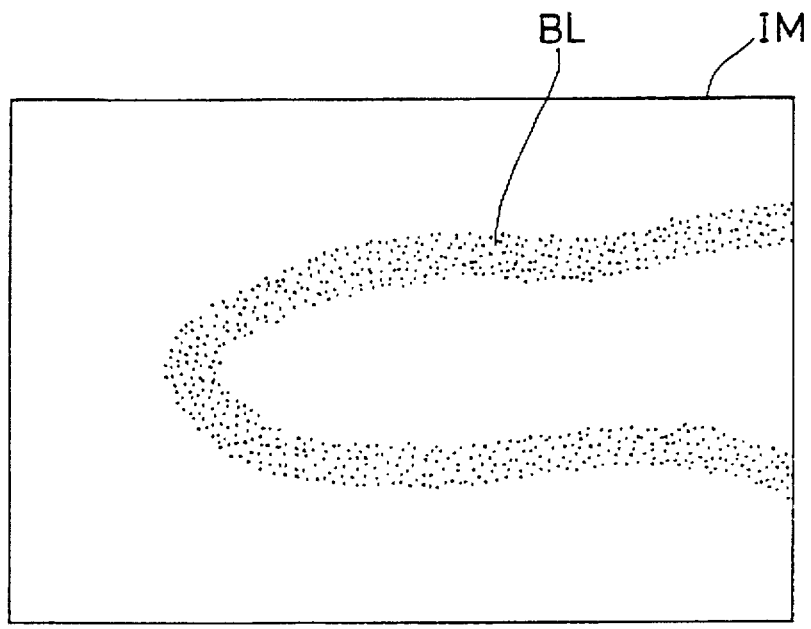
FIG. 3 is a view explaining the an example of an light intensity image obtained in embodiment.
Figure 4:
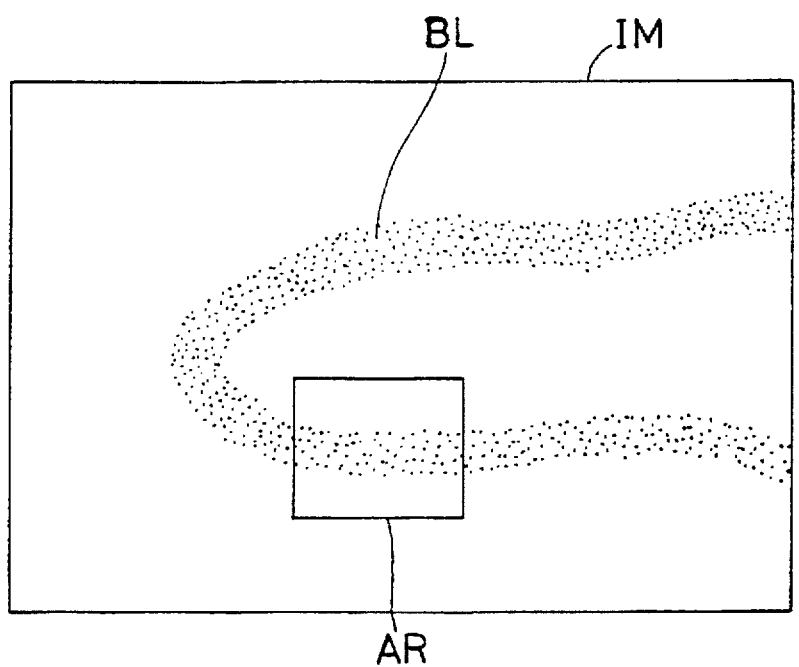
FIG. 4 is a view explaining a cut region of the image shown in FIG. 3.

A frame of an image IM containing a blood vessel BL is read as shown in FIG. 3 (step S1), followed by cutting a predetermined region AR (having, for example, 10×100 pixels) as shown in FIG. 4 (step S2).

Figure 5:
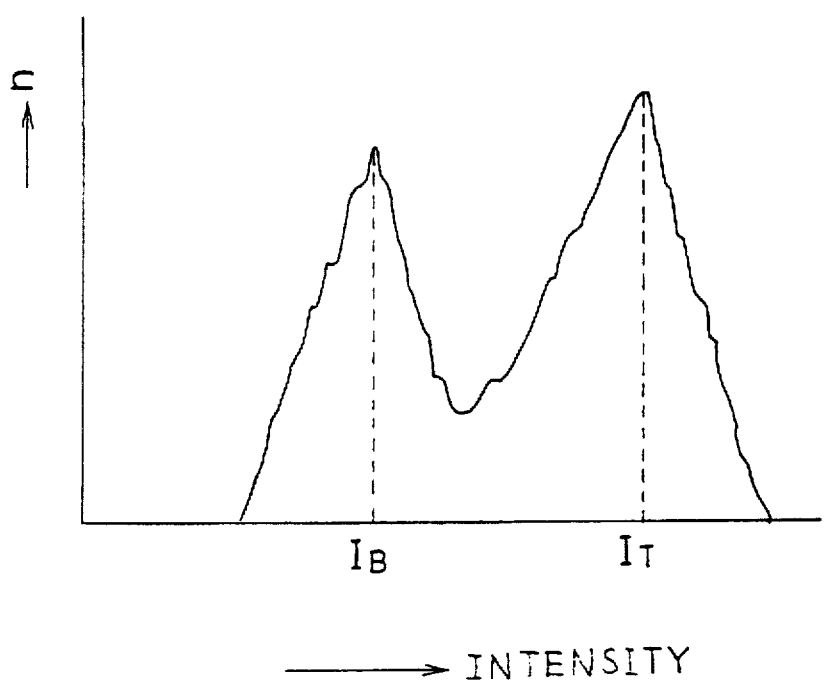
FIG. 5 is a histogram showing an example of a light intensity distribution of the image captured in the embodiment.

A distribution (histogram) of frequency of intensity of pixels of the predetermined region AR is prepared as shown in FIG. 5 (step S3), followed by detecting the lower intensity value as the light intensity $I_B$ of blood and the higher intensity value as the light intensity $I_T$ of the body tissue on the two maximum values of intensity (step S4).

The calculation of r=log ($I_T/I_B$) is performed (step S5), followed by determining the diameter D of the blood vessel BL from the image (step S6), performing the calculation of C=r/εD (step S7), and adding the value to Ct which is already calculated (step S8).

The above operation of S1 to S8 is repeated by the number of a plurality of frames, i.e., by the number F of frames (step S9), followed by calculating the mean value $C_{av}$ by dividing Ct by the number F of frames (step S10), and correcting the mean value $C_{av}$ obtained in capillary and small arteries and veins such that it is translated into the value corresponding to medium-size and large arteries and veins, thereby calculating the concentration of hemoglobin HGB (step S11). In practice, this operation is conducted based on a correction function experimentally obtained.

Measurement Embodiment

Blood vessels of the lips of a human being were imaged using the apparatus shown in FIG. 1, followed by measuring an intensity of scattered light $I_T$ of a body tissue and an intensity of scattered light $I_B$ of blood.

The imaging was performed such that incident light was applied on the blood vessels contained in the lips of the same human being, with the amount of the incident light varied at six stages.

Figure 6:
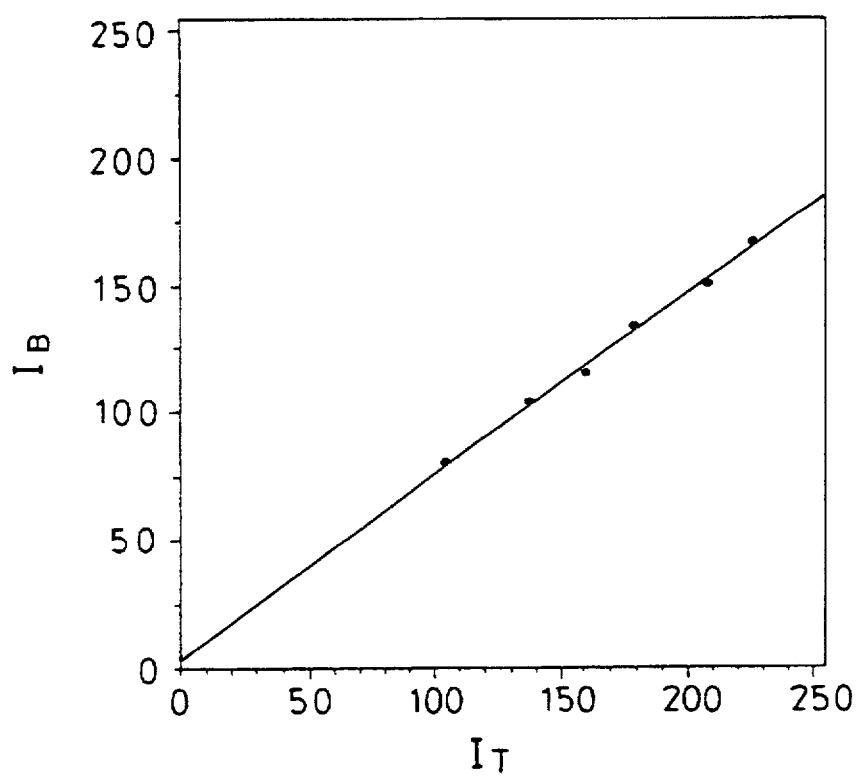
FIG. 6 is a graph showing the characteristics exhibited on measurement in the embodiment.

FIG. 6 shows the characteristics of the light intensity $I_T$ of blood and the light intensity $I_B$ of the body tissue when the amount of incident light applied on the blood was varied.

From FIG. 6, it is understood that the light intensity $I_B$ of blood over the light intensity $I_T$ of the body tissue is constant regardless of change in the amount of incident light, thus eliminating the need of calibrating the measured concentration of hemoglobin with respect to the intensity of the incident light.

An examination was made on the correlation between a concentration of hemoglobin HGB value X measured by a blood analyzer and a concentration of hemoglobin HGB value Y calculated in accordance with the present invention with respect to nine subjects having a hemoglobin value of 14 to 18 [g/dl]. The correlation coefficient was 0.861, thus proving that the apparatus of the present invention is sufficiently practical.

In accordance with the present invention, the concentration of hemoglobin can be measured using a light source having one wavelength (or one wavelength band), and eliminating the need of calibrating a concentration of hemoglobin depending on a light intensity.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for measuring a concentration of hemoglobin comprising:

light application means for applying light of a single wavelength or wavelength band to a detection region containing a blood vessel present in a living body;

image capturing means for capturing an image of the detection region to which the light is applied; and analysis means for analyzing the concentration of hemoglobin in blood flowing through the blood vessel by processing the captured image, the analysis means including light intensity detection means for detecting a light intensity of a body tissue and a light intensity of a region of blood flow from the captured image and calculating means for calculating the concentration of hemoglobin from a ratio of the detected light intensity of the body tissue relative to the detected light intensity of the region of blood flow.

2. The apparatus for measuring the concentration of hemoglobin of claim 1, wherein the analysis means further comprises blood vessel diameter detecting means for detecting a diameter of the blood vessel in the captured image and correction means for correcting the calculated concentration of hemoglobin based on the detected diameter of the blood vessel.

3. The apparatus for measuring the concentration of hemoglobin of claim 1, wherein the calculating means includes means for calculating a concentration C of hemoglobin from the following equation:

$$C = K \cdot \log(I_T/I_B)$$

wherein C represents a concentration of hemoglobin, $I_T$ represents a detected light intensity of a body tissue, $I_B$ represents a detected light intensity of the region of blood flow and K is a constant.

4. The apparatus for measuring the concentration of hemoglobin of claim 1, wherein the light intensity detecting means includes means for examining a frequency distribution of intensity of pixels in the captured image and means for detecting an intensity A as the light intensity of the region of blood flow and an intensity B as the light intensity of the body tissue, wherein the frequency distribution indicates peak values at the intensities A and B (A<B).

5. A method comprising the steps of:

applying light of a single wavelength or wavelength band to a detection region containing a blood vessel present in a living body;

capturing an image of the detection region to which the light is applied; and processing the captured image to measure a concentration of hemoglobin, wherein the step of processing the captured image includes the sub-steps of, detecting a light intensity of a body tissue and a light intensity of a region of blood flow from the captured image, and calculating the concentration of hemoglobin from a ratio of the detected light intensity of the body tissue relative to the detected light intensity of the region of blood flow.

6. The method for measuring the concentration of hemoglobin of claim 5, wherein the sub-step of calculating the concentration of hemoglobin further includes, detecting a diameter of the blood vessel in the captured image, and correcting the calculated concentration of hemoglobin based on the detected diameter of the blood vessel.

7. The method for measuring the concentration of hemoglobin of claim 5, wherein the sub-step of calculating the concentration of hemoglobin includes calculating the following equation:

$$C = K \cdot \log(I_T/I_B)$$

wherein C represents a concentration of hemoglobin, $I_T$ represents a detected light intensity of a body tissue, $I_B$ represents a detected light intensity of the region of blood flow and K is a constant.

8. The method for measuring the concentration of hemoglobin of claim 5, wherein the sub-step of detecting the light intensities of the body tissue and the region of blood flow includes detecting an intensity A as the light intensity of the region of blood flow and an intensity B as the light intensity of the body tissue wherein a frequency distribution on intensity of pixels in the captured image indicates peak values at the intensities A and B (A<B).

* * * * *